United States Patent [19]

Broad et al.

[11] Patent Number: 5,098,824
[45] Date of Patent: Mar. 24, 1992

[54] POLYNUCLEOTIDE PROBES FOR HORSES

[75] Inventors: Thomas E. Broad, Palmerston North; John W. Forrest, Renwick; Pauline E. Macdonald, Palmerston North; Patricia A. Pugh, Hamilton, all of New Zealand

[73] Assignee: Her Majesty the Queen in Right of New Zealand, Palmerston North, New Zealand

[21] Appl. No.: 382,986

[22] Filed: Jul. 21, 1989

[30] Foreign Application Priority Data

Jul. 21, 1988 [NZ] New Zealand .................. 225,513

[51] Int. Cl.$^5$ .............................. C12Q 1/68
[52] U.S. Cl. ........................... 435/6; 435/5; 436/501; 536/27; 536/28; 536/29; 935/6; 935/8; 935/76; 935/77; 935/78
[58] Field of Search ............. 435/6, 5; 436/501, 63, 436/94; 536/27, 28, 29; 935/6, 8, 76, 77, 78

[56] References Cited

FOREIGN PATENT DOCUMENTS 77388 7/1988 Australia .
2166445 5/1986 United Kingdom .

OTHER PUBLICATIONS

A. J. Jeffreys et al., "Hypervariable 'Minisatellite' Regions in Human DNA", *Nature* 314: 67–73 (1985).
A. J. Jeffreys et al., "DNA Fingerprints of Dogs and Cats", *Animal Genetics* 18: 1–15 (1987).
A. J. Jeffreys et al., "Mouse DNA 'Fingerprints': Analysis of Chromosome Localization and Germline Stability of Hypervariable Loci in Recombinant Imbred Strains", *Nucleic Acids Research* 15: 2823–2836 (1987).
A. J. Jeffreys et al., "The Implication of Hypervariable DNA-regions for Animal Identification", *Animal Genetics* 18 (Supplement 1): 141–142 (1987).
A. J. Jeffreys, "Highly Variable Minisatellites and DNA Fingerprints", *Biochemical Society Transactions* 15: 309–317 (1987).
G. Vassart et al., "A Sequence in M13 Phage Detects Hypervariable Minisatellites in Human and Animal DNA", *Science* 235, 683–684 (1987).
G. Vassart, "DNA Fingerprinting with Wild-Type M13 Bacteriophage as a Probe", *Trends in Genetics* 3 (No. 4): 89 (1987).
A. R. Wyman et al., "A Highly Polymorphic Locus in Human DNA", *Proc. Nat'l. Acad. Sci. U.S.A.* 77: 6754–6758 (1980).
G. I. Bell et al., "The Highly Polymorphic Region Near the Human Insulin Gene is Composed of Simple Tandemly Repeating Sequences", *Nature* 295: 31–35 (1982).
N. J. Proudfoot et al., "The Structure of the Human Zeta-Globin Gene and a Closely Linked, Nearly Identical Pseudogene", *Cell* 31: 553–563 (1982).
S. E. Y. Goodbourn et al., "Molecular Basis of Length Polymorphism in the Human Zeta-Globin Gene Complex", *Proc. Nat'l Acad. Science U.S.A.* 80: 5022–5026 (1983).
D. R. Higgs et al., "Highly Variable Regions of DNA Flank the Human α-Globin Genes", *Nucleic Acids Research* 9, 4213–4224 (1981).
Y. Nakamura et al., "Variable Number of Tandem Repeat (VNTR) Markers for Human Gene Mapping", *Science* 235: 1616–1622 (1987).
H. S. Shin et al., "An Unusual Coding Sequence from a Drosophila Clock Gene is Conserved in Vertebrates", *Nature* 317: 445–448 (1985).

(List continued on next page.)

Primary Examiner—Robert A. Wax
Assistant Examiner—Lori Yuan
Attorney, Agent, or Firm—Oliff & Berridge

[57] ABSTRACT

Isolated polynucleotide sequences capable of selectively hybridizing to fragments of Equidae DNA. Methods of identifying polymorphism in Equidae including extracting DNA, digesting the extracted DNA with a restriction enzyme, loading the digested DNA on a suitable gel and conducting electrophoresis, prehybridizing and hybridizing the digested DNA and determining the hypervariable regions in the digested DNA. A method of differentiating between the DNA of horses, donkeys or zebras from the DNA of other animals.

23 Claims, 5 Drawing Sheets

OTHER PUBLICATIONS

M. Georges et al., "DNA Fingerprinting in Man Using a Mouse Probe Related to Part of the Drosophila 'per' Gene", *Nucleic Acids Research* 15: 7193 (1987).

M. Georges et al., "DNA Fingerprinting in Domestic Animals Using Four Different Minisatellite Probes", *Cytogenet Cell Genet.* 47: 127-131 (1988).

A. P. Jarman et al., "Molecular Characterization of a Hypervariable Region Downstream of the Human Alpha-Globin Gene Cluster", *The EMBO Journal* 5: 1857-1863 (1986).

S. J. Fowler et al., "Use of a Hypervariable Region (HVR) Probe Alpha-Globin 3'HVR to Produce Individual Specific Fingerprints", *Genetical Res.* 52: 67 (1988).

J. C. S. Fowler et al., "Repetitive Deoxyribonucleic Acid (DNA) and Human Genome Variation—A Concise Review Relevant to Forensic Biology", *J. Forensic Science* 33: 1111-1126 (1988).

Z. Wong et al., "Characterization of a Panel of Highly Variable Minisatellites Cloned from Human DNA", *Ann. Hum. Genet.* 51: 269-288 (1987).

D. Troyer et al., "A Human Minisatellite Sequence Reveals DNA Polymorphism in the Equine Species", *J. Vet Med.* A. 36: 81-83 (1989).

N. J. Fraser et al., "Isolation and Characterization of a Human Variable Copy Number Tandem Repeat at Xcen-p11.22", *Genomics* 5: 144-148 (1989).

POLYNUCLEOTIDE PROBES FOR HORSES

FIELD OF INVENTION

This invention relates to polynucleotide probes useful for identifying polymorphism and pedigree in animals; and more particularly, polynucleotide probes useful for identifying polymorphism and pedigree in horses.

BACKGROUND

The technique of DNA fingerprinting is recognised to be capable of "revolutionising forensic biology".

The power of DNA fingerprinting technology is its potential to positively discriminate between closely related individuals and to determine pedigree. The probability that two related human individuals share the same DNA fingerprint is 1 in 100 million, except if they are identical twins. For unrelated individuals, the odds are even higher.

Apart from humans, horses are the other major species for which conventional blood-typing is widely established and accepted. Countries maintaining a stub book register of thoroughbred horses use about 20 polymorphic blood-typing systems to establish the identity of individuals and their pedigree. However, up to 4% of parentage cases of horses can not be satisfactorily resolved by these conventional blood-typing techniques.

Genetic fingerprinting consists broadly of the following aspects:

(a) Basis of genetic fingerprinting

It has been known for some years that there are hypervariable regions of DNA which show multiallelic variation. Those variable regions consist of tandem repeats of a short sequence, termed "minisatellites" which are stably inherited. Differences in the number of repeats provide the basis of polymorphism. Dr. Alec J. Jeffreys had discovered that many of such minisatellites have a high degree of homology and that certain core sequences are capable of seeking out of hybridising to more than one minisatellite. Such core sequences provide a powerful probe for revealing polymorphism and provide unique "fingerprints" for each individual.

(b) Application of the probe

Utilisation of probes involves the preparation of DNA in a suitable form and medium. The extracted DNA is cut by a suitable restriction enzyme into fragments of varying sizes. These fragments are separated by size by gel electrophoresis. The DNA fragments are then denatured and may or may not be transferred to a suitable medium by "blotting". The probe which has been tagged with a suitable marker or label is applied to the denatured fragments. The marker will then show up regions of hybridisation as bands which form the "fingerprint" of the DNA.

(c) Preferred criteria of a good DNA fingerprint (i) Bands should preferably be clearly visible.

(ii) Bands should preferably be distinct and clearly defined (from each other)

(iii) All bands should preferably be traceable to each parent.

(iv) In pedigree testing, there should preferably be at least 6 bands from each parent.

(v) The pattern of bands should preferably be specific or unique to each individual (except where the individual is an identical twin).

(vi) The bands should preferably be produced in DNA fragments greater than 1000 bp in length.

(vii) The bands should preferably be capable of detection using probes carrying both radioactive and non-radioactive labels.

(viii) The bands should preferably be capable of detection with less than saturating concentrations of probe.

(ix) The bands should preferably be capable of being produced from picogram quantities of DNA using DNA amplification procedures.

(d) Existing families of probes

It is suggested that the human genome might contain at least 1500 hypervariable regions (Jeffreys, A. J. (1987), Biochemical Society Transactions 15: 309–317). In UK Patent specification GB 2 166 445A, there is disclosed a family of probes derived from the 33 bp sequence in an intron of the human myoglobin. Other families of probes have been reported:

(i) a bacterium, Escherichia coli 'chi' sequence (Jeffreys, et, al, (1985) Nature 314: 67–73.

(ii) a bacteriophage, M13 sequence (Vassart, G., Georges, M., Monsieur, R., Brocas, H., Lequarre, A. S. & Christophe, D. (1987). Science, 235: 683–684).

(iii) a "simple quadruplet repeat (sqr)" sequence from snakes and other animals (Ali. S., Muller, C. R. and Epplen, J. T. (1986) Human Genetics 74: 239–243).

(iv) a human DNA library (Wyman, A. & White, R., (1980) Proc. Nat'l. Acad. Sci., U.S.A., 77: 6754–6758; Nakamura Y., Leppert, M., O'Connell, P., Wolff, R., Holm, T., Culver, M., Martin, C., Fujimoto, E., Hoff, M., Kumlin, E. and White, R. (1987) Science, 235: 1616-1622).

(v) a DNA sequence close to the human insulin gene (Bell G. I., Selby, M. J. and Rutter, W. J. (1982) Nature 295: 31–35).

(vi) DNA sequences close to the alpha-related globin genes, including myoglobin and zeta-globin (Proudfood N. J., Gil, A. & Maniatis, T. (1982). Cell, 31: 223–563; Goodbourne S. E. Y., Higgs, D. R., Clegg, J. B. and Weatherall, D. J. (1983) Proc. Natl. Acad, Sci., U.S.A., 80: 5022–5026; Higgs, D. R., Goodbourn, S. E. Y., Wainscoat, J. S., Clegg, J. B. and Weatherall, D. J. (1981). Nucleic Acids Res. 9: 4213–4224).

(vii) Sequences near the human Harvey-ras oncogene (Capon D. J., Chen E. Y., Levinson, A. D., Seeberg, P. H. and Goeddel, D. V. Nature, 302: 33–37).

(viii) the X-gene region of the hepatitis B virus (Nakamura Y., Leppert, M., O'Connell, P., Wolff, R., Holm, T., Culver, M., Martin, C., Fujimoto, E., Hoff, M., Kumlin, E. and White, R. (1987) Science, 235: 1616-1622).

(ix) Drosophila 'Per' gene (Shin, H. S., Bargiello, T. A., Clarke, B. T., Jackson, F. R. and Young, M. W. (1985) Nature 317: 445–4419; Georges, M., Lequarre, A-S, Castelli, M., Hanset, R. & Vassart, G. (1988) Cytogenetics & Cell Genetics, 47: 127-131).

(x) human satellite III sequence (Fowler, C., Drinkwater, R., Burgoyne, L., Skinner, J. (1987) Nucl. Acids Res. 15: 3929).

Some of these probes have been tested in relation to humans with different results and degrees of success under similar conditions (Vassart, 1987, supra). The resulting DNA fingerprint is sensitive to the sequence of the repeats and within a family, different probes which vary slightly in their 'core' sequence detect almost completely different sets of hypervariable regions to produce different fingerprint patterns (Jeffreys 1987, supra).

(e) Cross-species hybridisation

It is recognised that the genetic fingerprinting technique is not limited to human use. Cross-species nucleic acid hybridisation is well-known and various families of probes196ve been used on species other than that from which the probe was derived. In the UK Patent Specification 2, 166, 445A, it was stated that the probe derived from the human myoglobin gene has been tested in economically-important animals such as dogs, cats, sheep, pigs, horses and cattle with varying degrees of success. In particular, it was stated that the fingerprint obtained from the use of the most promising probe on horses and pigs "are faint [and] contain very few bands compared with the corresponding human DNA fingerprints". This was also stated in Jeffreys, A. J., Hillel, J., Hartley, N., Bulfield D. B., Wilson, V. & Harris, S. (1987) Animal Genetics, 18 (Supplement 1): 141–142.

EXPERIMENTS WITH HUMAN, HORSES AND SHEEP DNA

Various restriction enzyme digests of genomic DNA of goats, sheep, human and cows were hybridised with genomic sheep and horse DNA fragments which were nick translated using the technique described by Ken C. Reed and David A. Mann (Efficient Nick Translation of DNA. Dept. of Biochemistry, Faculty of Science, Australian National University). The results show that there is neglige cross-hybridisation between horse DNA fragments and those of human or other animals tested. Similar results were obtained when various restriction enzyme digests of genomic DNA were probed with nick translated sheep DNA fragments.

Although the mechanics of hybridisation are not fully understood, it appears that there is some degree of specificity in relation to individual species to obtain clear results in similar conditions. In particular, equine DNA stood out as being obviously different from cow, goat, sheep and human.

DESCRIPTION OF THE INVENTION

A fundamental study of repetitive DNA sequences of horses has detected major families of repetitive DNA sequences in horse. This was done in two ways:
(a) It is known that some of the enzymes -Alu, Sau, Taq- produce families of repetitive sequences in the mammalian genome. The horse DNA was digested with these various enzymes, electrophoresed in agarose gels and probed with $^{32}$P-nick translated horse DNA.
(b) Hybridisation bands were also detected using nick translated genomic DNA as probes or probes of individual repeats.

It was observed that under conditions where minisatellite bands of sheep and goats were detected following hybridisation with sheep DNA, no distinct minisatellite bands were seen in horse DNA hybridised with itself. To obtain distinct bands for horse DNA, certain experimental conditions were preferred, in particular:
(i) the type of restriction enzymes and;
(ii) the concentration of the target DNA; and
(iii) the gel concentration.

Higher DNA concentration and gel concentration were preferred for the detection of minisatellite bands in horse DNA than in sheep DNA, leading to the conclusion that minisatellites are present in the horse DNA at a lower level than in the sheep DNA. We have also identified various restriction enzymes which produced particularly useful results in detecting the minisatellites. Using these restriction enzymes, we have then sought to detect, isolate and clone a family of repeats which will be suitable for the construction of a proble. Our preliminary approach in this search was to narrow the list of suitable restriction enzymes. The horse DNA was cut to completion using the various restriction enzymes. Each group of digested horse DNA was cloned separately. It was expected that since replication of recombinant plasmids is reduced when they contain foreign DNA inserts of greater than 5 kb in length, and that since there will be a higher proportion of repeat sequence in the low-copy DNA fragments than unique sequence, this approach would provide a relatively fast and convenient method of producing cloned repeats.

The plasmids pUC18 and pUC19 (Yanisch-Perron, C., Vieiva, J. and Messing, J. (1985) Gene 33: 103–119) were used and the horse DNA fragments were cloned into the polylinker site immediately adjacent to the lac z-gene. The recombinant plasmids were then transferred into the *Escherichia coli* K12 strain JM109 where it was able to replicate. *E. coli* JM109 is a rec A-strain which is less likely to eliminate repetitive DNA inserts (Miller, H., (1987) *Methods in Enzymology* 152: 145–170). The insertion of the DNA in the *E. coli* disrupts the lac z-gene which codes for the enzyme B-galactosidase. As a result, the *E. coli* is unable to metabolise 5-bromo-4-chloro-3-indolyl-$\beta$-D-galactoside (Xgal) and the colonies appear on plates containing Xgal as white rather than blue colonies.

A selection of up to 200 white colonies were routinely subcultured in 96-well microtitre plates. Aliquots from these cultures were dot blotted onto nylon membranes after rapid lysis/DNA extration in 0.4M NaOH. The procedure followed that described by Ken C. Reed and Klaus I. Matthaei, Rapid Dot Blot Analysis of Specific DNA Sequences in Tissue Samples by Alkaline Digestion and Fixation to Nylon Membrane (Dept. of Biochemistry, Faculty of Science, Australian National University).

The dot-blotted membranes were then hybridised to $^{32}$P-nick translated horse DNA and autoradiographed. There were some intense dots as well as moderate to faint dots. The majority however did not show hybridisation, indicating the absence of repeat DNA sequence fragments. The intensely hybridising dots were expected to contain horse DNA sequence that either:
(a) were representative of the most frequently occurring families of repeated sequences or
(b) contained tandem arrays of less frequently occuring repeats; the tandem arrays contributing to the hybridisation intensity.

Representatives of the intensely hybridising colonies, moderate to weak colonies and some non-hybridising colonies were selected and individually propagated. The DNA was extracted and run on 0.8% gel to determine the size of the recombinant plasmid. The plasmid DNA was then cut with restriction enzymes to remove the insert, electrophoresed and transferred to nylon membranes. These were then hybridised to $^{32}$P-nick translated horse DNA to:
(a) confirm that they were authentic horse fragments:
(b) estimate their size; and
(c) determine, by their hybridisation intensity, whether they are likely to be high, medium or low-copy repeats.

Having regard to these considerations, and to the ability to grow efficiently and to retain its inserted DNA, we selected 5–10 clones from each restriction digest.

The selected repeats from each family (which is based an individual restriction enzyme digest) provided individual inserts which were used as probes. These were hybridised to the different families of repeats, providing a cross-referencing system which showed similarities and differences between the repeats.

We discovered that there were two major families:
(i) Sau-like family, and
(ii) Taq-like family.

The Sau family hybridised to families from Hae III, Pvu II, Fok I, Ban II and Msp I.

The Taq family hybridised to families from Rsa I, Hinf I, Ava II, Alu I, Kpn I and Hind II.

The distinction is not entirely clear cut and is blurred by 'overlapping' repeats.

As we have narrowed the search to these two (Sau-like and Taq-like) families of probes, representatives from each family were hybridised to genomic horse DNA cut with various restriction enzymes, run on gels (1-2%) and transferred to nylon membrane. Samples which showed predominant hybridisation to low molecular weight fragments (<4 kb) were discarded as being unlikely to produce fingerprints. Those which produced bands showing hybridisation were retained. The minisatellite bands were either cut out of the gel and electrophoretically removed or run onto NA45 membrane and subsequently eluted. The minisatellite bands were purified and subsequently cloned. These were sequenced to determined their molecular structure.

We derived a molecular sequence from the Taq clone termed E4/1 which is 702 base pairs long and composed of 32 reiterated 'core sequences' of 21 base pairs long useful for detecting polymorphism in equine DNA.

The consensus sequence of one strand of the core is as follows:

| | G | - | G | C | A | G | G | T | G | G | T | T | C | C | G | G | C | A | T | G | T | C |
|---|---|---|---|---|---|---|---|---|---|---|---|---|---|---|---|---|---|---|---|---|---|---|
| % | 72 | 53 | 75 | 72 | 97 | 72 | 88 | 97 | 91 | 63 | 97 | 94 | 84 | 59 | 78 | 88 | 66 | 47 | 75 | 78 | 56 | 72 |
| position | 1 | 2 | 3 | 4 | 5 | 6 | 7 | 8 | 9 | 10 | 11 | 12 | 13 | 14 | 15 | 16 | 17 | 18 | 19 | 20 | 21 | 22 |

The production of good 'fingerprints' depends upon a suitable probe sequence and optimal hybridisation conditions. Essentially, a stable adduct between the target DNA minisatellite and the probe is required.

The derivation of the E4/1 sequence and the core sequence is the key to obtaining a suitable probe sequence and forms the basis of this invention. In particular, the core sequence may be altered or varied to obtain desired results in fingerprinting trials. The invention, in its broadest form, thus consists of the following:

Polynucleotides having the general formula, read in the 5'-3' sense:

$$N.(core)_a.M$$

where 'core' represents a sequence having at least 6 consecutive nucleotides, selected from within any of the following sequences read in the same order:

G- GCA GGT GGT TCC GGC ATG TC-
GX GCA GGT GGT TCY GGC ATG TCZ
JX GKA GLT GGT TCY OGP STU VWZ where X is A or -
Y is C or T
Z is - or C
J is G or C
K is C or -
L is G or A
O is G or A
P is C, A or T
S is A, G or C
U is G or A
V is T, C or G
W is C or T a is equal to or greater than 1;
N and M represents 0, 1 or greater than 1 flanking nucleotide(s);

and where a is greater than 1, the repeating 'core' sequence must show at least 70% homology to the original core sequence and the repeating 'core' sequence need not have the same length or sequence, and the complementary sequence to the original sequence defined above.

In another form, the invention consists of the following:

Polynucleotides having the general formula, read in the 5'-3' sense:

$$N.(J.core.K)_a.M$$

where 'core' represents a sequence having at least 6 consecutive nucleotides, selected from within any of the following sequences read in the same order:

G- GCA GGT GGT TCC GGC ATG TC-
GX GCA GGT GGT TCY GGC ATG TCZ where
X is A or -
Y is C or T
Z is - or C a is equal to or greater than 1;
J and K represents 0 to 15 additional nucleotide(s) within the repeating sequence
N and M represents 0, 1 or greater than 1 flanking nucleotide(s); and where a is greater than 1, the repeating 'core' sequence must show at least 70% homology to the original core sequence and the repeating (J.core.K) sequence need not have the same length or sequence,
and the complementary sequence to the original sequence defined above.

An embodiment of the invention comprises polynucleotides as defined above where 'core' represents the consensus sequence of E4/1.

A preferred embodiment of the invention is where the 'core' represents the following sequence:

AGG TGG TTC AGG TGG TTC

A further preferred embodiment of the invention is where the 'core' represents the following sequence:

CTG AAC CAC CTG AAC CAC

A further preferred embodiment of the invention is where the 'core' represents the following sequence:

GGC AGG TTG TTC CGT TGT GCT T

Another preferred embodiment of the invention is where the 'core' represents the following sequence:

GGC AGG TGG TTC CGG CAT GTC

A preferred preferred embodiment of the invention is where the 'core' represents the following sequence:

GTG GTT CCG GCA TGT CGG CA

A particularly preferred embodiment of the invention is where the 'core' represents the above specified sequences and a is 1 or 2.

Another preferred embodiment of the invention is the complete sequence of E4/1. It was noted that there is considerable variation between the 32 repeated 'core sequences' in the E4/1 molecule. The appearances of various bases in the consensus sequence vary from a high percentage of 97% (positions 5, 8 and 11) to 47% (position 18). The following shows the percentages of appearances of other bases which are above 10%:

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|----|----|----|----|----|----|----|----|----|----|----|----|----|----|
|   | C | A | - |   |   |   |   |   | A  |    |    |    | T  | A  |    | A  | C  |    | A  | C  | T  | T  |
| % | 25 | 41 | 19 |   |   |   |   |   | 22 |    |    |    | 34 | 19 |    | 16 | 12 |    | 13 | 25 | 22 | 28 |
|   |   |   | C |   |   |   |   |   |    |    |    |    |    |    |    | T  | G  | C  |    | G  |    | C  |
| % |   |   | 13 |   |   |   |   |   |    |    |    |    |    |    |    | 16 | 25 | 16 |    | 13 |    | 31 |

Positions in any repeat sequence where the highest rate of appearance of any base is 60% or less may be termed as ambiguous positions.

Such variation will produce a mismatch with the consensus sequence resulting in an unstable adduct. It may thus be expected that a single or low copy repeat unit of the consensus sequence or some variation of it will not have 100% efficiency in hybridising to repeat units in the horse DNA due to such mismatch. One solution is to use an appropriate base analog that can "pair" with any of the four natural bases at the ambiguous position. One suitable compound which was proposed is 2'-deoxyinosine (E. Ohtsuko, et. al., *J. Biol. Chem.* 260(5), p. 2605-2608). Another compound which pairs to adenosine and guanosine ambiquities is 5-Fluorodeoxyuridine (J. F. Habener, et. al., *Proc. Natl. Acad. Sci. U.S.A.* (Biochemistry) 85, pp. 1735-1739). It was also reported that hybrid duplexes containing A-F and G-F base pairs show more stability than duplexes containing A-T and G-C base pairs.

Accordingly, a preferred form of the invention consists of:

Polynucleotides having the general formula, read in the 5'-3' sense:

$N.(core)_a.M$ where 'core' represents a sequence having at least 6 consecutive nucleotides, selected from within any of the following sequences read in the same order:

G- GCA GGT GGT TCC GGC ATG TC-
GX GCA GGT GGT TCY GGC ATG TCZ where
X is A or -
Y is C or T
Z is - or C
provided that up to 50% of the 'core' nucleotides may be replaced with any compound capable of pairing with one or more of the four natural bases;
a is equal to or greater than 1;
N and M represents 0, 1 or greater than 1 flanking nucleotide(s);
and where a is greater than 1, the repeating 'core' sequence must show at least 70% homology to the original core sequence and the repeating 'core' sequence need not have the same length or sequence,
and the complementary sequence to the original sequence defined above.

A further embodiment of the invention consists of the following:

Polynucleotides having the general formula, read in the 5'-3' sense:

$N.(J.core.K)_a.M$ where 'core' represents a sequence having at least 6 consecutive nucleotides, selected from within any of the following sequences read in the same order:

G- GCA GGT GGT TCC GGC ATG TC-
GX GCA GGT GGT TCY GGC ATG TCZ where
X is A or -
Y is C or T
Z is - or C
provided that up to 50% of the 'core' nucleotides may be replaced with any compound capable of pairing with one or more of the four natural bases;
and where a, N, M, J and K are as previously defined, and the complementary sequence to the above.

A preferred embodiment of the invention consists of polynucleotides as defined above where the replacement of 'core' nucleotide by any compound capable of pairing with one or more of the four natural bases occurs at ambiguous positions.

A particularly preferred embodiment of the invention consists of where the replacement compound is 2'-deoxyinosine.

Another preferred embodiment of the invention consists of where the replacement compound is 5'-Fluorodeoxyuridine.

By using the natural consensus core sequence or any of its variants, it is possible to derive further repeat sequences which may be referred to as "second generation sequences" which are suitable for use as a probe. It is hence a further apart of this invention to use the natural consensus sequence or any of the variations as described aforesaid to derive further repeat sequences suitable for use as a probe to identify polymorphism and pedigree in animals.

In particular, a preferred embodiment of this invention consists of polynucleotides having the general formula, read in the 5'-3' sense:

$$N.(J.core.K)_a.M$$

where the 'core' represents a sequence having at least 6 consecutive nucleotides, selected from a consensus sequence obtained from the identification of hypervariable repeat sequences using polynucleotides as previously defined. Furthermore, a similar process may be carried out using such 'second generation' polynucleotides to derive 'third generation' polynucleotides.

It is also a preferred aspect of the invention to consist of polynucleotides which 'core' sequence is derived from any second generation repeat sequence where bases at ambiguous position or positions in the sequence is replaced with any compound capable of pairing with one or more of the four natural basis. The invention also consists of the construction of the polynucleotide of the invention as hereinbefore described.

It is expected that the consensus core sequence is specific to horses although the variants and second generation sequences may not be. Accordingly, a particular aspect of the invention comprises the use of the polynucleotide of the invention as hereinbefore described to identify polymorphism and pedigree in animals. More particularly, the invention comprises the use of the polynucleotide of the invention as hereinbefore described to identify polymorphism and pedigree in horses. In another aspect the invention consists of a method of identifying polymorphism and pedigree in animals using a polynucleotide as defined herein comprising the steps of DNA extraction, digestion of the extracted DNA with restriction enzyme, electrophoresis on a suitable gel, prehybridisation and hybridisation with the polynucleotide or polynucleotides, washing, autoradiography and analysis of the results.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

CONDITIONS OF OPERATION

In our experiments, it became clear that hybridisation is affected by any change in condition. The optimal condition is a function of many factors, including the probe sequence, the number of reiteration, the length of the sequence, the length of the probe, the A-T:G-C ratio and the relative number of minisatellites in the host. We have discovered that only a range of restriction enzymes which do not cut within the core sequence of the repeats provide the necessary fragments.

A second consideration in the stability of the adduct is the melting temperature. It is recognised that A-T base pairs melt preferentially to G-C base pairs. As a result, probes with a high G-C content have traditionally been favoured. A solution was proposed (W. I. Wood, *Proc. Natl. Acad. Sci. U.S.A.* 82, pp. 1585-1588) where hybridization in the presence of or where hybridisation is followed by washing with tetramethylammonium chloride which binds to and stabilises the A-T base pairs. Other derivatives such as tetraethyl and tetralkyl of ammonium chloride will be similarly effective.

(i) Hybridisation conditions

Early experiments established that the simple conditions of Ken Reed produced hybridisation of comparable to greater sensitivity to that which was described by Dr. A. J. Jeffreys.

| Ken Reed conditions were: | |
| --- | --- |
| hybridisation/pre-hybridisation solution: | 1.5 × SSPE |
| | 7% SDS |
| | 0.5% dried milk powder |
| probe concentration: | 5 ng/ml. |
| temperature: | 68 degrees Celsius |
| time: | 4 hrs. prehybridisation, about 16 hrs. (overnight) hybridisation |
| washing: 1. | 2 × SSC, 0.1% SDS 15' @ room temperature |
| 2. | 2 × SSC, 0.1% SDS 15' @ room temperature |
| 3. | 0.5 × SSC, 0.1% SDS 15' @ room temperature |
| 4. | 0.1 × SSC, 0.1% SDS 30' @ 50 degrees Celsius |

| Jeffreys conditions were: | |
| --- | --- |
| Prehybridisation: | 3 × SSC wash, then wash in hybridisation solution |
| Hybridisation solution: | Denhardts (Ficoll, PVP, BSA), 1 × SSC; SDS 0.1%; 6% PEG, 1 µg/ml human placental DNA. |
| Probe concentration: | 2-25 ng/ml |
| Temperature: | 65 degrees Celsius |
| Washing: | 1. 6 × hybridisation solution; 40 min. @ 65 degrees Celsius, |
| | 2. 0.1 × SSC, 0.1% SDS, 50 µg/ml. salmon sperm DNA for 30 min. @ 65 degrees Celsius |
| | 3. 3 × SSC |

We subsequently discovered from the use of the polynucleotide probes that the CRE protocol was more satisfactory than either of the above procedures.

| CRE Protocol: | |
| --- | --- |
| hybridisation/ pre-hybridisation solution: | 1.5 × SSPE 1% SDS |

| CRE Protocol: | -continued |
| --- | --- |
| | 6% PEG |
| | 0.5% dried milk powder |
| Probe concentration: | 0.1–10.0 ng/ml. |
| Temperature: | 61 degrees Celsius |
| Washing: | 1. 3 × SSC, 0.1% SDS @ 61 degrees Celsius rinses until control strips of blot have < 5 cps |
| | 2. repeat with (1.) but extend washing period to 5' |
| | 3. 1 × SSC, 0.1% SDS @ 61 degrees Celsius for 10' repeating three to four times |

Further experimentation with the polynucleotide probes showed that the *Church & Gilbert Protocol* (as described by Church, G. M. & Gilbert, W. (1984) Proc. Natl. Acad. Sci. U.S.A. 81: 1991–1995, or as modified by Westneat, D. F., Noon, W. A., Reeve, H. K. and Aquadro, C. F. (1988) Nucl. Acids Res., 16: 4161) was also satisfactory in producing informative fingerprints.

| Church & Gilbert Protocol | |
| --- | --- |
| Hybridisation and prehybridisation solution: | 1% bovine serum albumin |
| | 1 mM EDTA |
| | 0.5M NaHPO$_4$, pH 7.2 |
| | 7% NaDodSO$_4$ (SDS) |
| | or 5 × SSC rinse followed by |
| | 7% SDS |
| | 1 mM EDTA, pH 8.0 |
| | 0.263M, Na$_2$HPO$_4$ |
| | 1% BSA |
| Probe concentration: | 0.1–10 ng/ml |
| Temperature: | 60–65° Celsius |
| Washing: 1. | 15 min. 2 × SSC, 0.1% SDS at room temperature. repeat |
| 2. | as in (1) at 60° Celcius |
| 3. | rinse in 1 × SSC |

For large complex probes, optimal time for DNA hybridisation is predicted from the general equation:

$$[1/\text{weight of probe } (\mu g)] \times [\text{length of probe (kb)}/5] \times [\text{volume of hybridisation (ml)}/10 \times 2] =$$

number of hours for optimal result.

However for short polynucleotide probes, it is known that the length and composition of the probe both affect the optimal temperature of hybridisation occurring to the general formula:

$$T_{hyb.} = 2(\text{no. of } A-T\ bp) + 4(\text{no. of } G-C\ bp) - 5$$

Therefore, ranges of temperatures were tested to determine their effect on:
(i) the complexity of the fingerprinting produced (as the temperature is increased, we expect less hybridisation and fewer bands);
(ii) the intensity of the background (non specific) reaction (as the temperature is reduced, we expect more non-specific binding and less distinct fingerprints).
The temperature ranges tested:
20 degrees Celsius (room temperature)
35 degrees Celsius
45 degrees Celsius
50 degrees Celsius
55 degrees Celsius
60 degrees Celsius
65 degrees Celsius
70 degrees Celsius.

(2) Probe labelling conditions

Early experiments were performed using nick translated probes using alpha-$^{32}$P dNTPd (prepared using Ken Reed procedure). These are known to cause 'networking' reaction which can lead to diffuse bands and increased backgrounds. Subsequently, as we began working with polynucleotide probes (for which the nick translated procedure was no longer an efficient method for labelling) we started using the random primer extension procedure. This is based on using the Amersham random oligonucleotide primer kits. The primer is typically a hexanucleotide (6 bases) of random sequence and produce our best results. Shorter polynucleotide probes were labelled using [gamma-$^{32}$P] ATP following the methods of Ken Reed.

METHOD

DNA from horse, human, sheep, pig, cow, goat, zebra and donkey leukocytes was extracted by conventional procedures as described in Maniatis, T., Fritsch, E. F. and Sambrook, J. (1982) Molecular Cloning, A Laboratory Manual. Cold Spring Harbour, N.Y. DNA molecular weight standards were purchased from Bethesda Research Laboratories.

Five micrograms of genomic DNA was digested with HaeIII (New England Biolabs) according to other maker's recommended procedures, and then loaded onto submarine, horizontal, 0.6% agarose gels (20 cm × 25 cm × 0.4 cm) in Tris-borate EDTA buffer. Electrophoresis was at 1.5 V/cm for 17 h at room temperature. The gels were then stained in 0.5 micrograms/ml ethidium bromide for 1 h, and photographed under short-wavelength UV light. Neutralisation, denaturation and subsequent transfer of the DNA from the gel to nylon membranes was essentially by the conventional Southern procedure. After transfer, the membranes were washed in 2×SSC, blotted dry and hybridised with the probe.

Two probes were used: (a) E4/1, a naturally occurring minisatellite fragment that we isolated from horse DNA and (b) JF-7, a 21-nucleotide oligomer of the consensus repeat sequence of E4/1.

The E4/1 probe was labelled with either alpha $^{32}$P-dCTP (3,000 Ci/mmole. New England Nuclear) or $^{35}$S-dATP using the random primer procedure described by Feinberg, AP and Vogelstein, B. (1983), Analytical Biochemistry 132:6–13, to an average specific activity of 2×10$^9$ dpm/ug. The oligonucleotide probe JF-7 was end-labelled with [gamma-$^{32}$P]-ATP following the method of Ken Reed.

After prehybridisation, hybridisation and washing following the CRE protocol, the membranes were then placed on Fuji RX X-ray film at −20° C. for 6 hours to 4 day, and the autoradiograms developed.

RESULTS

Five sets of DNA fingerprints are shown. On each, the position of BRL molecular weight markers are indicated.

BRIEF DESCRIPTION OF THE PHOTOGRAPHS

GGC AGG TGG TTC CGG CAT GTC.

EXAMPLE 1

This example illustrates the specificity of the probe of the invention to hybridise to regions in the DNA of Equidae, but not to the DNA of other domestic animal species.

DNA samples were prepared from the blood of human, goat, zebra, horse, donkey, pig, sheep and cow; digesed, electrophoresed, blotted and hybridised at 65° Celsius in 1×SSC to the horse probe E4/1 as described previously.

Figure 1:
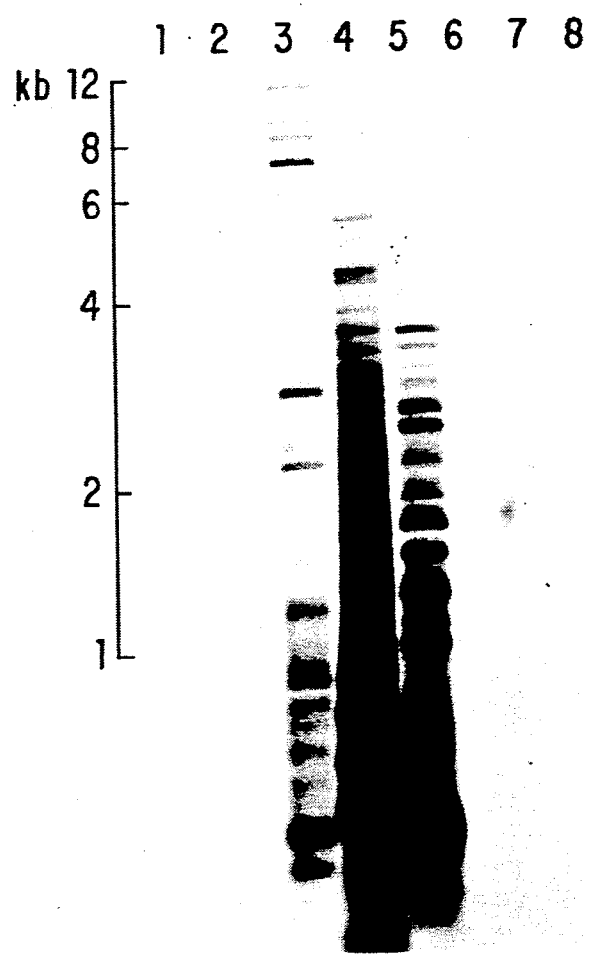
FIG. 1 is a photocopy of a photograph of an autoradiograph of general DNA fragments from various mammals hybridising to the horse probe E4/1.

The results shown in FIG. 1, are with the following samples:
1. human DNA
2. goat DNA
3. zebra DNA
4. horse DNA
5. donkey DNA
6. pig DNA
7. sheep DNA
8. cow DNA.

Fingerprint-like patterns were obtained only with zebra, horse and donkey DNA, but not from any of the other vertebrates tested, demonstrating the Equidae-specific nature of the horse probe.

Possible applications of this specificity include commercial testing of meet and processed meat products, and forensic screening of blood stains for species or origin.

EXAMPLE 2

The use of the probe to detect hypervariable regions in DNA of horses.

DNA samples were prepared from the blood of eight horses and hybridised at 65° Celsius in 1×SSC to the horse probe E4/1 as previously described.

Figure 2:
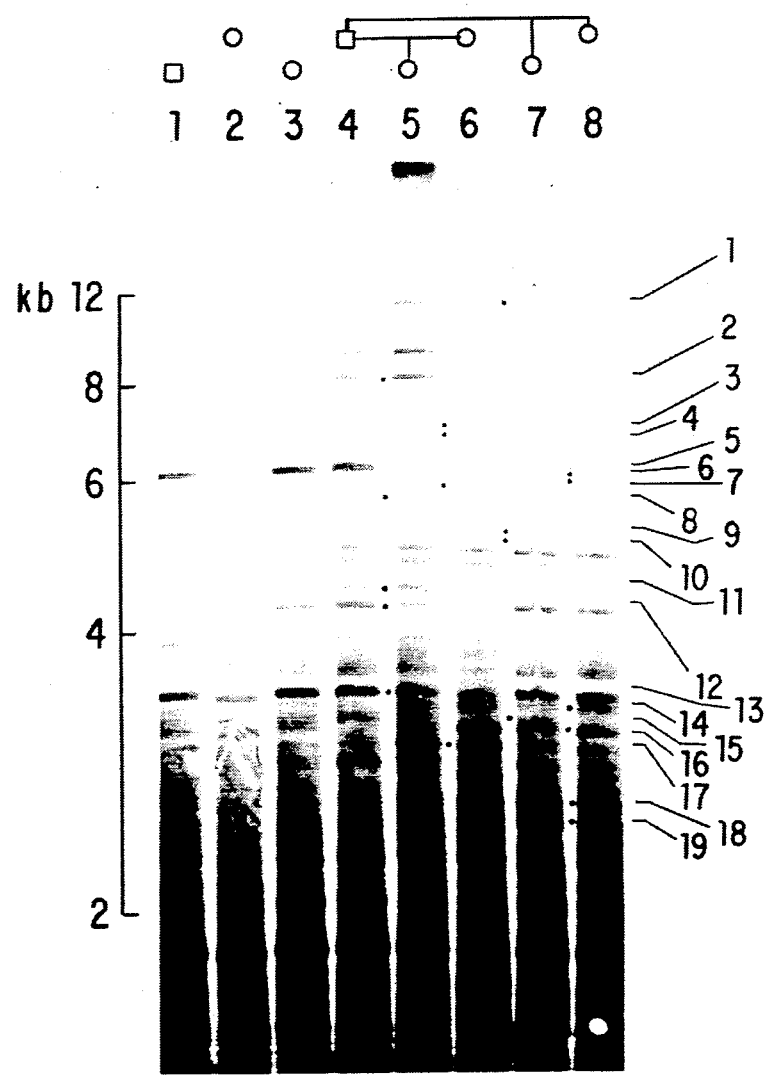
FIG. 2 is a photocopy of a photograph of an autoradiograph of the DNA from eight related and unrelated horses hybridised with the horse probe E4/1.

FIG. 2 illustrates the complex profile of hybridising fragments in the DNA of different horses, particularly in the 3–12 kb region. Several bands, e.g., band numbered 1, 5, 10 and 13 are commonly in over half of the horses shown. This might be expected from the Equidae-specific nature of the probe.

EXAMPLE 3

The use of the probe in pedigree-analysis of horses.

Figure 3:
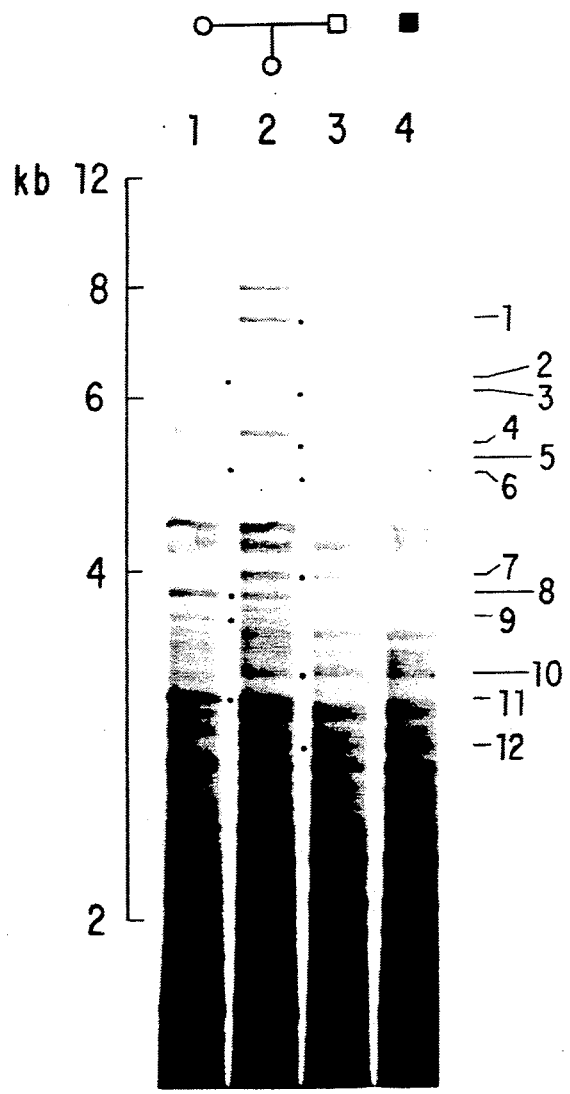
FIG. 3 is a photocopy of a photograph of an autoradiograph of the DNA from three related and one unrelated hybridised with the horses probe E4/1.
Figure 4:
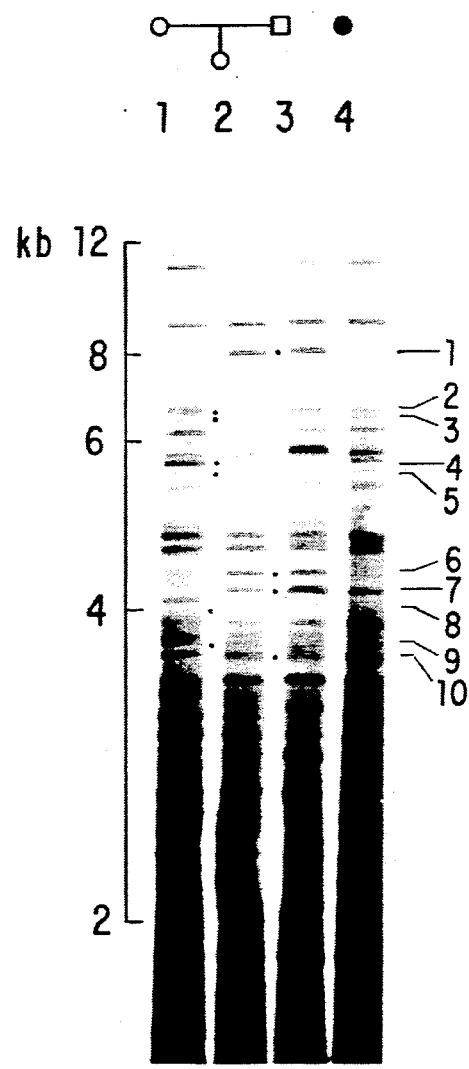
FIG. 4 is a photocopy of a photograph of an autoradiograph of the DNA from a different set of three related and one unrelated horses hybridised with the horse probe E4/1.

DNA fingerprinting profiles produced by the horse probe E4/1 in different families of horses are shown in FIGS. 2, 3 and 4.

DNA samples from the blood or related and unrelated horses were prepared and hybridised at 65° Celsius to the probe E4/1 as previously described.

In FIG. 2, DNA fingerprint hands in the two female offspring (lanes 5 and 7) that originate in the stallion (lane 4) and their respective mares (lanes 6 and 8) are indicated. In one of the offspring (lane 5), fingerprint band numbers 2, 8, 11, 12 and 13, are inherited only from the stallion (lane 4). The following bands are inherited only from the dam (mare, lane 6); band numbers 3, 4, 6, 7 and 17.

In the other offspring (lane 7), bands inherited only from the stallion (lane 4) are numbers 1, 9, 10 and 15: those from the dam (mare, lane 8) are numbers 5, 6, 14, 16, 18 and 19.

In FIG. 3, a single horse family is illustrated which is unrelated to the families in FIGS. 2 and 4. The offspring (lane 2) has the following DNA fingerprint bands which are inherited only from its father (stallion, lane 3): band numbers 1, 3, 4, 6, 7, 10 and 12. The following bands are inherited only from its mother (mare, lane 1): band numbers 2, 5, 8, 9 and 11.

In FIG. 4, another horse family is illustrated, unrelated to the family in FIG. 3, but comprising the mare (lane 6) and the stallion (lane 4) in FIG. 2 but with a different offspring. The DNA fingerprint bands in the offspring (lane 2) which are paternally inherited only (stallion, lane 3) are as follows: band numbers 1, 6, 7 and 10. Bands inherited only from the mother (mare, lane 1) are: band numbers 2, 3, 4, 5, 8 and 9.

EXAMPLE 4

Discovery that oligonulceotide probes derived from the sequence of the horse probe can be used in the pedigree-analysis of horses.

Figure 5:
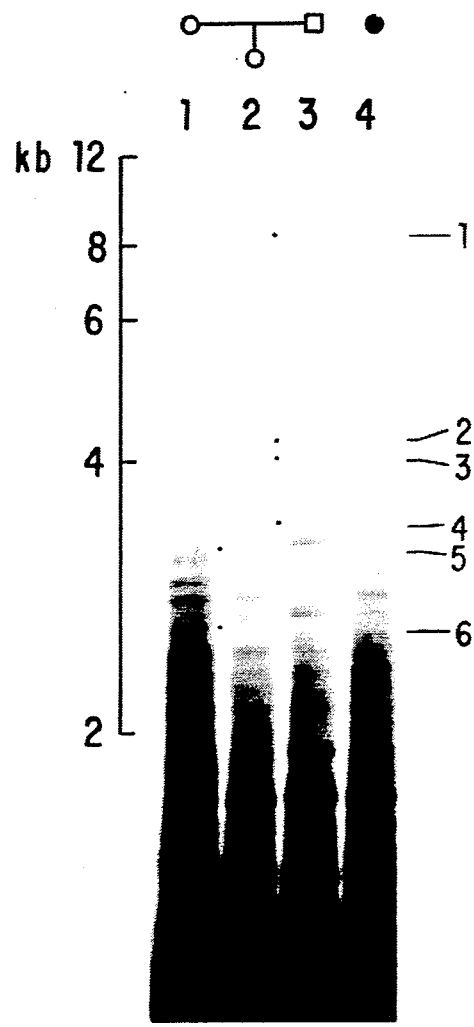
FIG. 5 is a photocopy of a photograph of an autoradiograph of the DNA from the same horses as in FIG. 4 hybridised with the oligonucleotide probe JF-7 having the following sequence.

DNA samples from the same group of horses whose DNA fingerprints are shown in FIG. 4, were hybridised to the oligonucleotide probe JF-7 as described previously. The hydridisation stringency was 50° in 3×SSC. The results shown in FIG. 5 illustrate that the oligonucleotide probe produces the same general DNA fingerprint profile as the horse probe E4/1. However, the intensity of hybridisation to the large molecular weight fragments is noticeably less than with E4/1.

In the offspring (lane 2), band numbers 1, 2, 3 and 4 are from the stallion (lane 3) while band numbers 5 and 6 are inherited maternally (mare, lane 1).

This data indicates that an oligonucleotide which comprises a single repeat is sufficient to produce a DNA fingerprint profile in horses, and can be used in the analysis of parentage.

MOLECULAR SEQUENCE OF E 4/1

| 1 | 11 | 21 | 31 | 41 | 51 |
|---|----|----|----|----|----|
| CGAGCAGGTG | GTTCCGGCGT | GCTCGGCTGG | TGCTTCCGGG | GTCATTGGCA | CGGGGTTCTG |
| 61 | 71 | 81 | 91 | 101 | 111 |
| GCATGTCTGA | GAGGTGGTTC | CTGCATGCCC | GGCAAGTGAT | TCCGGAGTGT | TCGCCAAGTG |
| 121 | 131 | 141 | 151 | 161 | 171 |
| GTTCTGGCAT | AGTCGGCAGG | TGATTTTGGC | ATGTCCGGCA | GTGGTTCAGG | CCAGTTGAGC |

-continued
MOLECULAR SEQUENCE OF E 4/1

| 181 AGGTGGTTCC | 191 AACGTGCTTG | 201 GCAGGTGCTT | 211 CCGGCGTCTC | 221 CGGCACGTGT | 231 TTCTGGCACA |
| --- | --- | --- | --- | --- | --- |
| 241 TCTGACAGGT | 251 GGTTCCGGTA | 261 TGCCCGAAAG | 271 GTGATTGCGG | 281 TCTGTCCGGT | 291 AGTGGTTCCA |
| 301 GCCTGCACGG | 311 CATGTGGTTC | 321 TGGTACGTCT | 331 CAGAGGTGGT | 341 TGCGCATGCC | 351 CAACAGGTGA |
| 361 TTCCGGACTG | 371 TCCGCCACAT | 381 GGTTCTGGCA | 391 CGTCTGAGAG | 401 GCTGGTTCCG | 411 GCATGCCGGC |
| 421 AGGTCATGCC | 431 AGAGAGTCCT | 441 CCAACTGGTT | 451 CTGGCATAAC | 461 ACGCAGGTGA | 471 ATTTTGGCGT |
| 481 GTCTGGCAGG | 491 TTGTTCCGTT | 501 GTGCTTGGCA | 511 GGTGGTTCAG | 521 GCTTGGCCGG | 531 CAGGTGAGTT |
| 541 CCAGACTGTC | 551 CAGGACGTGT | 561 TTCCAGCTTC | 571 TCCGGCAGGT | 581 GGTTCTGGTA | 591 CGTCTGAGAG |
| 601 GTGGTTCCGC | 611 CATGGCTGGC | 621 AGGTGATTCC | 631 GGACCGTCCC | 641 CCAGGTGGTT | 651 CTGGCATAGC |
| 661 CAGCAGTTAA | 671 TATTGGCCTG | 681 TCCGGAGGTG | 691 GTTCCAGCAA | 701 GT | |

What we claim is:

1. An isolated polynucleotide consisting essentially of a sequence selected from the following core sequences read in the 5'-3' sense:

```
G— GCA GGT GGT TCC GGC ATG TC—,
GX GCA GGT GGT TCY GGC ATG TCZ,
JX GKA GLT GGT TCY OGP STU VWZ,
CTG AAC CAC CTG AAC CAC,
GGC AGG TTG TTC CGT TGT GCT T,
J GGC AGG TGG TTC CGG CAT GTT Z, and
GTG GTT CCG GCA TGT CGG CA,
``` where
X is A or -
Y is C or T
Z is - or C
J is G or C
K is C or -
L is G or A
O is G or A
P is C, A or T
S is A, G or C
U is G or A
V is T, C or G
W is C or T or any sequence complementary thereto, said polynucleotide being capable of selectively hybridizing to fragments of Equidae DNA wherein the symbol "-" represents the absence of a nucleotide without creating a gap in the sequence.

2. The polynucleotide as claimed in claim 1, consisting essentially of a sequence selected from the following core sequences read in the 5'-3' sense:

```
G— GCA GGT GGT TCC GGC ATG TC—
GX GCA GGT GGT TCY GGC ATG TCZ
``` where
X is A or -
Y is C or T
Z is - or C or any sequence complementary thereto wherein the symbol "-" represents the absence of a nucleotide without creating a gap in the sequence.

3. The polynucleotide as claimed in claim 1, wherein said core sequence is

G- GCA GGT GGT TCC GGC ATC TCor any sequence complementary thereto wherein the symbol "-" represents the absence of a nucleotide without creating a gap in the sequence.

4. The polynucleotide as claimed in claim 1, wherein said core sequence is

GX GCA GGT GGT TCY GGC ATG TCZ or any sequence complementary thereto.

5. The polynucleotide as claimed in claim 1, wherein said core sequence is

JX GKA GGT GGT TCA GGT GGT TCZ or any sequence complementary thereto.

6. The polynucleotide as claimed in claim 1, consisting essentially of the following sequence:

CTG AAC CAC CTG AAC CAC or any sequence complementary thereto.

7. The polynucleotide as claimed in claim 1, consisting essentially of the following sequence:

GGC AGG TTG TTC CGT TGT GCT T or any sequence complementary thereto.

8. The polynucleotide as claimed in claim 1, wherein said core sequence is:

J GGC AGG TGG TTC CGG CAT GTT Z or any sequence complementary thereto.

9. The polynucleotide as claimed in claim 1, wherein said core sequence is:

GTG GTT CCG GCA TGT CGG CA or any sequence complementary thereto.

10. An isolated polynucleotide consisting essentially of the following sequence:

| 1 | 11 | 21 | 31 | 41 | 51 |
|---|---|---|---|---|---|
| CGAGCAGGTG | GTTCCGGCGT | GCTCGGCTGG | TGCTTCCGGG | GTCATTGGCA | CGGGGTTCTG |
| 61 | 71 | 81 | 91 | 101 | 111 |
| GCATGTCTGA | GAGGTGGTTC | CTGCATGCCC | GGCAAGTGAT | TCCGGAGTGT | TCGCCAAGTG |
| 121 | 131 | 141 | 151 | 161 | 171 |
| GTTCTGGCAT | AGTCGGCAGG | TGATTTTGGC | ATGTCCGGCA | GTGGTTCAGG | CCAGTTGAGC |
| 181 | 191 | 201 | 211 | 221 | 231 |
| AGGTGGTTCC | AACGTGCTTG | GCAGGTGCTT | CCGGCGTCTC | CGGCACGTGT | TTCTGGCACA |
| 241 | 251 | 261 | 271 | 281 | 291 |
| TCTGACAGGT | GGTTCCGGTA | TGCCCGAAAG | GTGATTGCGG | TCTGTCCGGT | AGTGGTTCCA |
| 301 | 311 | 321 | 331 | 341 | 351 |
| GCCTGCACGG | CATGTGGTTC | TGGTACGTCT | CAGAGGTGGT | TGCGCATGCC | CAACAGGTGA |
| 361 | 371 | 381 | 391 | 401 | 411 |
| TTCCGGACTG | TCCGCCACAT | GGTTCTGGCA | CGTCTGAGAG | GCTGGTTCCG | GCATGCCGGC |
| 421 | 431 | 441 | 451 | 461 | 471 |
| AGGTCATGCC | AGAGAGTCCT | CCAACTGGTT | CTGGCATAAC | ACGCAGGTGA | ATTTTGGCGT |
| 481 | 491 | 501 | 511 | 521 | 531 |
| GTCTGGCAGG | TTGTTCCGTT | GTGCTTGGCA | GGTGGTTCAG | GCTTGGCCGG | CAGGTGAGTT |
| 541 | 551 | 561 | 571 | 581 | 591 |
| CCAGACTGTC | CAGGACGTGT | TTCCAGCTTC | TCCGGCAGGT | GGTTCTGGTA | CGTCTGAGAG |
| 601 | 611 | 621 | 631 | 641 | 651 |
| GTGGTTCCGC | CATGGCTGGC | AGGTGATTCC | GGACCGTCCC | CCAGGTGGTT | CTGGCATAGC |
| 661 | 671 | 681 | 691 | 701 | |
| CAGCAGTTAA | TATTGGCCTG | TCCGGAGGTG | GTTCCAGCAA | GT | | or any sequence complementary thereto, said polynucleotide being capable of selectively hybridizing to fragments of Equidae DNA.

11. The polynucleotide as claimed in claim 1, wherein up to 50% of the nucleotides in said core sequence are replaced with any replacement compound functional as a nucleotide substitute and capable of pairing with one or more of the four natural bases.

12. The polynucleotide as claimed in claim 2, wherein up to 50% of the nucleotides in said core sequence are replaced with any replacement compound functional as a nucleotide substitute and capable of pairing with one or more of the four natural bases.

13. The polynucleotide as claimed in claim 10, wherein up to 50% of the nucleotides are replaced with any replacement compound functional as a nucleotide substitute and capable of pairing with one or more of the four natural bases.

14. The polynucleotide as claimed in claim 13, wherein the replacement compound capable of pairing with one or more of the four natural bases is 2'-deoxyinosine.

15. The polynucleotide as claimed in claim 14, wherein said sequence includes the core sequence:

GX GCA GGT GG TT CC GG CI TG TC where I is 2'-deoxyinosine
or any sequence complementary thereto.

16. The polynucleotide as claimed in claim 13 wherein the replacement compound capable of pairing with one or more of the four natural bases is 5'-fluorodeoxyuridine.

17. The polynucleotide according to claim 1, wherein said polynucleotide is a probe.

18. The polynucleotide according to claim 2, wherein said polynucleotide is a probe.

19. The polynucleotide according to claim 10, wherein said polynucleotide is a probe.

20. An isolated polynulceotide consisting essentially of the following sequence:

AGG TGG TTC AGG TGG TTC or any sequence complementary thereto, said polynucleotide being capable of selectively hybridizing to fragments of Equidae DNA.

21. An isolated polynucleotide consisting essentially of the following sequence:

GGC AGG TGG TTC CGG CAT GTC or any sequence complementary thereto, said polynucleotide being capable of selectively hybridizing to fragments of Equidae DNA.

22. A method of identifying polymorphism in Equidae, consisting essentially of:
extracting DNA;
digesting the extracted DNA with a restriction enzyme which does not cut the following core sequences of polynucleotides:

G— GCA GGT GGT TCC GGC ATG TC—,
GX GCA GGT GGT TCY GGC ATG TCZ,
J X GKA GLT GGT TCY OGP STU VWZ,
CTG AAC CAC CTG AAC CAC,
GGC AGG TTG TTC CGT TGT GCT T,
J GGC AGG TGG TTC CGG CAT GTT Z, and -continued
GTG GTT CCG GCA TGT CGG CA, where
X is A or -
Y is C or T
Z is - or C
J is G or C
K is C or -
L is G or A
O is G or A
P is C, A or T
S is A, G or C
U is G or A
V is T, C or G
W is C or TC; wherein the symbol "-" represents the absence of a nucleotide without creating a gap in the sequence loading the digested DNA on a suitable gel and conducting electrophoresis;

prehybridizing and hybridizing the digested DNA with said polynucleotide or polynucleotides which have been labelled or marked; and determining hypervariable regions in the digested DNA.

23. A method of differentiating between the DNA of horses, donkeys or zebras from the DNA of other animals, consisting essentially of:

extracting DNA;

digesting the extracted DNA with a restriction enzyme which does not cut the following core sequences of polynucleotides:

G— GCA GGT GGT TCC GGC ATG TC—,
GX GCA GGT GGT TCY GGC ATG TCZ,
JX GKA GLT GGT TCY OGP STU VWZ,
CTG AAC CAC CTG AAC CAC,
GGC AGG TTG TTC CGT TGT GCT T,
J GGC AGG TGG TTC CGG CAT GTT Z, and
GTG GTT CCG GCA TGT CGG CA, where
X is A or -
Y is C or T
Z is - or C
J is G or C
K is C or -
L is G or A
O is G or A
P is C, A or T
S is A, G or C
U is G or A
V is T, C or G
W is C or T; wherein the symbol "-" represents the absence of a nucleotide without creating a gap in the sequence conducting electrophoresis on said digested DNA on a suitable gel;

prehybridizing and hybridizing the digested DNA with said polynulceotide or polynucleotides which have been labeled or marked; and determining if said polynucleotide hybridized with said DNA.

* * * * *